United States Patent [19]

Nishizawa et al.

[11] Patent Number: 5,470,154
[45] Date of Patent: Nov. 28, 1995

[54] METHOD OF CLEANING THE REFLECTOR MIRROR IN AN OPTICAL DEW POINT METER AND AN OPTICAL DEW POINT METER EQUIPPED WITH A CLEANING DEVICE

[75] Inventors: Junichi Nishizawa, Miyagi; Takahiko Kijima, Hyogo, both of Japan; Edward F. Ezell, Warren, N.J.; Akira Makihara, Chiba, Japan

[73] Assignee: Osaka Sanso Kogyo Ltd., Japan

[21] Appl. No.: 299,883

[22] Filed: Sep. 1, 1994

Related U.S. Application Data

[63] Continuation of Ser. No. 993,235, Dec. 17, 1992, abandoned.

[30] Foreign Application Priority Data

Apr. 18, 1991 [JP] Japan ............................. 3-086900
Dec. 1, 1991 [JP] Japan ............................. 3-357408

[51] Int. Cl.⁶ ..................... G01N 25/68; G01N 21/47; G01N 21/55; B08B 5/00
[52] U.S. Cl. ..................... 374/141; 134/11; 134/31; 374/17; 374/20
[58] Field of Search ............... 134/11, 31; 374/17, 374/18, 19, 20, 28, 27, 141; 73/29.01

[56] References Cited

U.S. PATENT DOCUMENTS

| | | | |
|---|---|---|---|
| 2,893,237 | 7/1959 | Coriolis et al. | 374/20 |
| 3,623,356 | 11/1971 | Bisberg | 374/20 |
| 4,155,245 | 5/1979 | Coe . | |
| 4,216,669 | 8/1980 | Harding, Jr. . | |
| 4,345,455 | 8/1982 | Hayes, Jr. | 374/20 |
| 4,629,333 | 12/1986 | Dosoretz et al. | 374/20 |
| 4,972,677 | 11/1990 | Moriya et al. . | |
| 5,052,818 | 10/1991 | Nishizawa et al. | 374/17 |
| 5,068,040 | 11/1991 | Jackson | 134/31 |
| 5,201,960 | 4/1993 | Starov | 134/11 |

FOREIGN PATENT DOCUMENTS

| | | | |
|---|---|---|---|
| 345215 | 12/1989 | European Pat. Off. . | |
| 409546 | 1/1991 | European Pat. Off. . | |
| 0874231 | 10/1981 | U.S.S.R. | 134/31 |
| 2224639 | 5/1990 | United Kingdom | 134/11 |
| 84/02291 | 12/1984 | WIPO . | |

*Primary Examiner*—Diego F. F. Gutierrez
*Attorney, Agent, or Firm*—Roylance, Abrams, Berdo & Goodman

[57] ABSTRACT

A method of cleaning a reflector mirror in an optical dew point meter that measures the dew point or frost point of a sample gas by a process including the steps of bringing the sample gas into contact with the reflector mirror whose temperature is variable, projecting condensed rays of light or laser light onto said reflector mirror, and detecting the change in the intensity of scattered light and/or reflected light on account of the dew or frost formed on said reflector mirror, characterized by bringing a $CO_2$ gas or a $CO_2$ containing gas into contact with the reflector while the latter is in a cooled state, thereby condensing $CO_2$ on the surface of the reflector mirror, and the subsequent step of heating the reflector mirror to vaporize the $CO_2$ is dischosed.

6 Claims, 9 Drawing Sheets

METHOD OF CLEANING THE REFLECTOR MIRROR IN AN OPTICAL DEW POINT METER AND AN OPTICAL DEW POINT METER EQUIPPED WITH A CLEANING DEVICE

This is a continuation of application Ser. No. 07/993,235, filed Dec. 17, 1992, now abandoned, which is a continuation of international application Ser. No. PCT/JP92/00493, filed Apr. 17, 1992.

FIELD OF THE INVENTION

The present invention relates to a method of cleaning the reflector mirror in optical dew point meter, and also relates to an optical dew point meter equipped with a cleaning device.

BACKGROUND OF THE INVENTION

Conventionally known optical dew point meters are designed such that a chilling means such as a multi-stage Peltier device and a Freon freezer or a liquid nitrogen or helium refrigerator is combined with a heater means to thereby permit the varying of the temperature of a reflector mirror to the subliming point of $CO_2$ and below. When a sample gas is brought into contact with said reflector mirror, and followed by the projection of condensed rays of light or laser light onto dew or frost formed on the reflector mirror, the change in the intensity of the resulting scattered light and/or reflected light caused by varying of the temperature of the reflector mirror can be detected and it is possible to know the dew point or frost point of the sample gas and to thereby determine its water content. A major problem of these optical dew point meters is that the reflector mirror is fouled by fine particles, oil components, etc. during continued measurements. In particular, the precision, sensitivity and detection limit for the measurement of dew point or frost point are greatly influenced if the reflector mirror is fouled. Many proposals have been made on the basis of many years of studies conducted on the method of cleaning a fouled reflector mirror but it has been difficult to retain satisfactory precision after cleaning.

For example, U.S. Pat. No. 3,623,356 describes a method in which the temperature at the surface of a reflector mirror is elevated periodically to the dew point or higher, whereby all dew or frost is evaporated from the reflector mirror and, thereafter, the degree of fouling of the reflector mirror is checked before starting the cleaning operation. Japanese Patent Public Disclosure Nos. 154652/1981 and 151347/1981 proposed methods for continuous measurement. In those methods, the value for a reflector mirror is corrected on the basis of the degree of fouling of a reference plane that is close to tile reflector mirror and which is maintained at a higher constant temperature and if the degree of fouling of the reference plane is found to have reached a certain value, the reflector mirror is cleaned by heating it above the dew point. However, these methods are intended to achieve a certain recovery of the reflectance of the mirror, not to a level completely equal to the reflectance as measured when making quality inspection before shipment from the factory. In order to achieve complete recovery to the initial reflectance, the reflector mirror has to be returned to the factory for readjustment at considerable cost.

A further problem with the optical dew point meter is that it is airtight in the interior. If it is disassembled for cleaning, it must be reassembled and this is a cumbersome operation. In addition, the reassembled instrument must be tested for airtightness. Because of the need to perform these operations, the cleaning of the dew point meter necessitates its shutdown for a period of from at least one week to one month.

Instead of disassembling it, one may contact the reflector mirror with a gas containing the vapor of a cleaning organic solvent. This method is also capable of cleaning the reflector mirror but it is not easy to prepare a suitable organic solvent of high quality. In addition, the organic solvent used will build up in the airtight chamber and it takes considerable time to remove it by evaporation. Of course, cleaning with Freon is also effective but its use should be restricted to preserve the atmospheric environment and from safety and hygenic view-point.

SUMMARY OF THE INVENTION

The present invention solves the aforementioned problems of the prior art by contacting a fouled mirror with a $CO_2$ gas or a $CO_2$ containing gas whereby the $CO_2$ is condensed and evaporated.

In accordance with a first embodiment, the present invention relates to a method of cleaning a reflector mirror in an optical dew point meter that measures the dew point or frost point of a sample gas by a process including the steps of bringing the sample gas into contact with the reflector mirror whose temperature is variable, projecting condensed rays of light or laser light onto said reflector mirror, and detecting the change in the intensity of scattered light and/or reflected light on account of the dew or frost formed on said reflector mirror, which method is characterized in that said method includes the step of bringing a $CO_2$ gas or a $CO_2$ containing gas into contact with the reflector while the latter is in a cooled state, thereby condensing $CO_2$ on the surface of the reflector mirror, and the subsequent step of heating the reflector mirror to vaporize the $CO_2$.

In accordance with a second embodiment, the present invention relates to an optical dew point meter equipped with a cleaning device, said meter comprising:

(i) a reflector mirror whose temperature is variable;
(ii) a gas inlet or a gas blowing nozzle for supplying a sample gas into a compartment including said reflector mirror in such a way that said sample gas will contact said reflector mirror;
(iii) a means of projecting condensed rays of light to that part of the reflector mirror where dew or frost is to form;
(iv) a mechanism for detecting the change in the intensity of scattered light and/or reflected light due to the dew or frost formed on the reflector mirror;
(v) a mechanism for sensing that the capability of detecting a normal change in the intensity of reflected light and/or scattered light has decreased on account of the fouling of the reflector mirror;
(vi) a mechanism for causing the $CO_2$ or $CO_2$ containing gas to contact the reflector mirror either automatically or manually; and
(vii) a mechanism for detecting the temperature at which the change in the intensity of scattered light and/or reflected light was detected.

In accordance with a third embodiment, the present invention relates to the removal of impurities contained in the $CO_2$ containing gas, more particularly to a process for preparing a pure gas suitable for use, as well as a method of removing unsuitable impurities.

DETAILED DESCRIPTION OF THE INVENTION

The present invention is described below in detail with reference to the no-limiting accompanying drawings. The dew point meters shown in the drawings are for illustrative purposes only and the present invention is by no means limited to those dew point meters.

Figure 1:
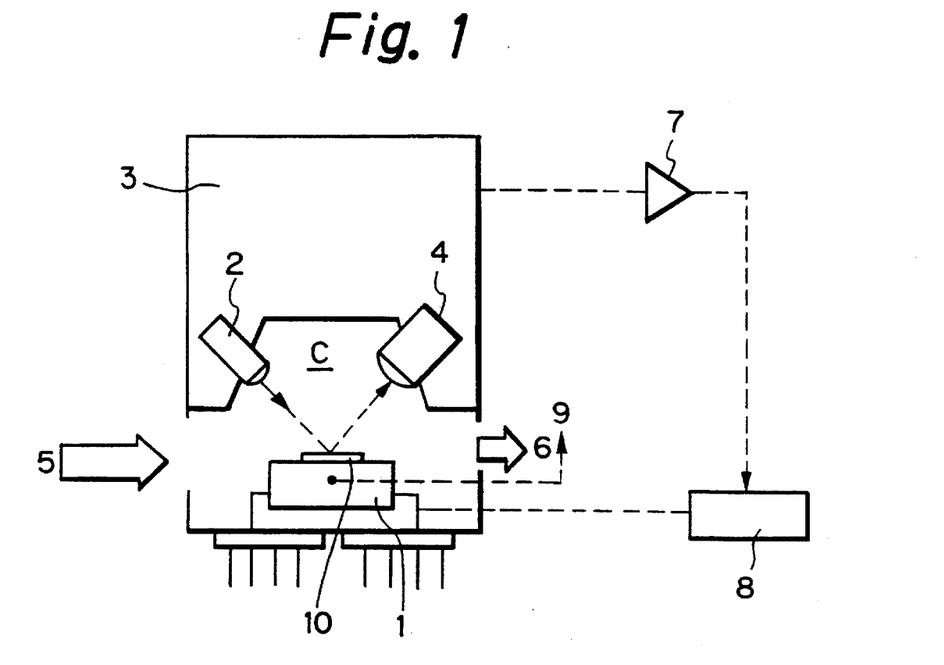
FIG. 1 is a diagram showing an apparatus according to a preferred embodiment of the present invention.
Figure 2:
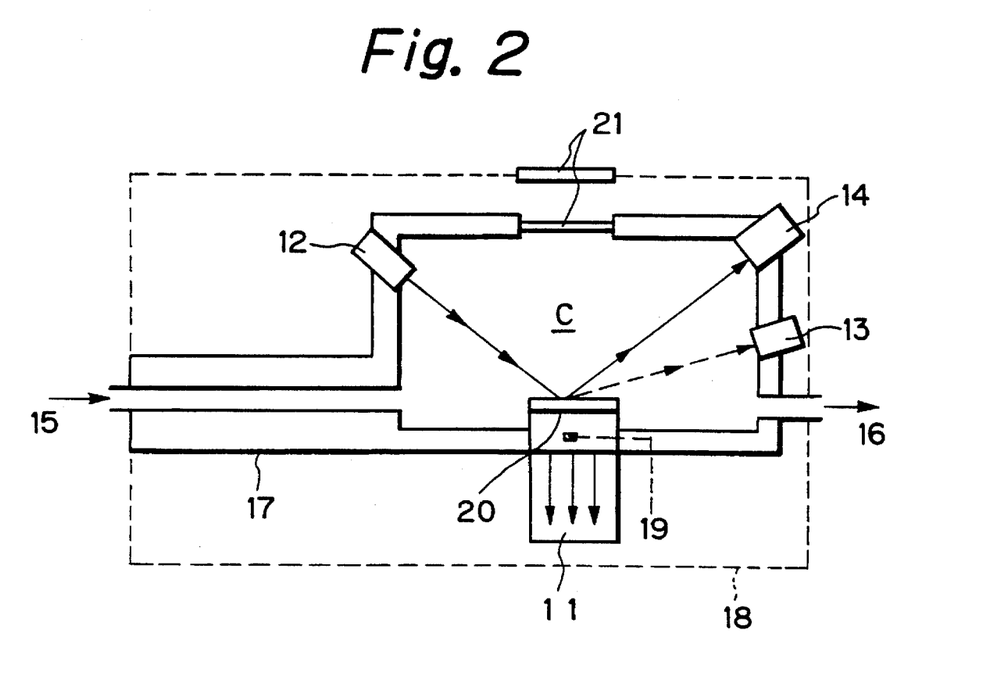
FIG. 2 is a diagram showing an apparatus according to another preferred embodiment of the present invention.
Figure 3:
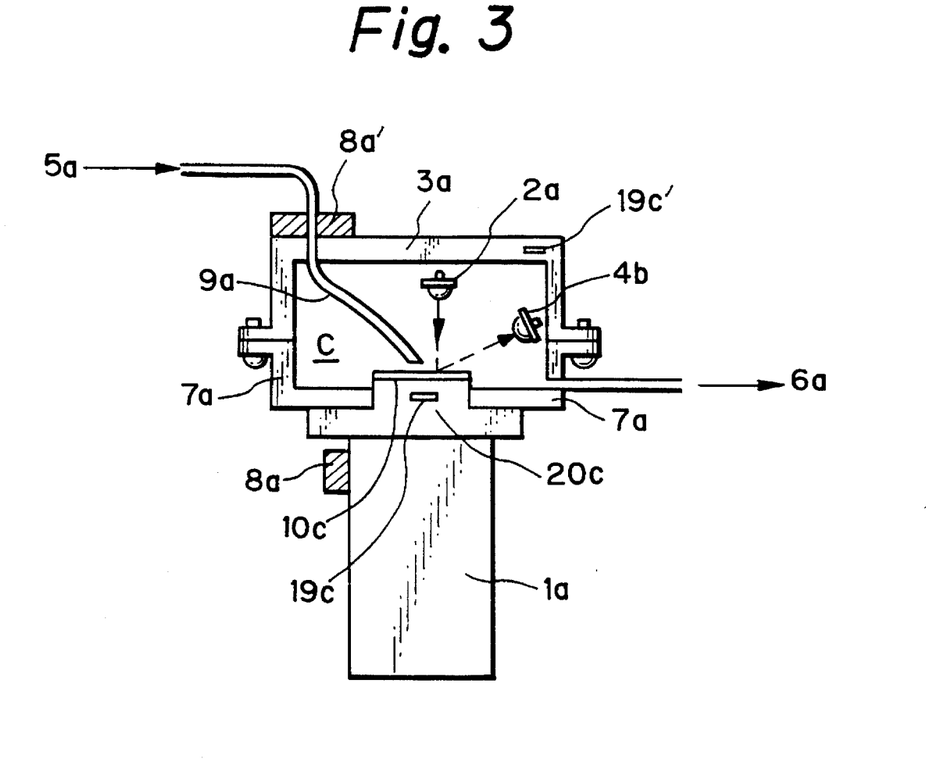
FIG. 3 is a diagram showing an apparatus according to still another preferred embodiment of the present invention.
Figure 4:
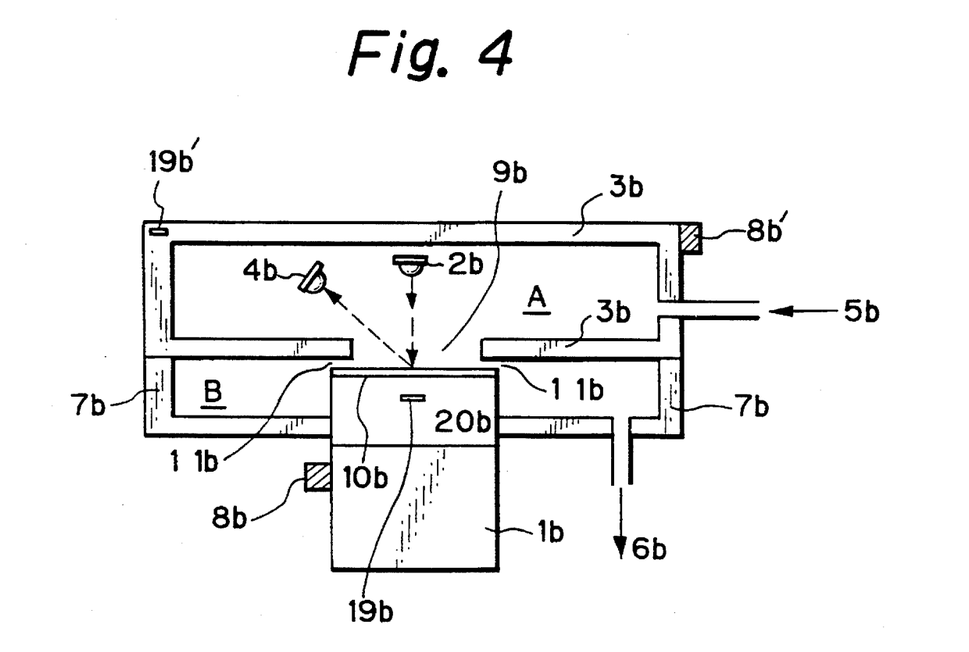
FIG. 4 is a diagram showing an apparatus according to yet another preferred embodiment of the present invention.

FIG. 1 shows a dew point meter of reflection type that measures the water content on the basis of the change in the intensity of reflected light; FIG. 2 shows a dew point meter that measures the water content on the basis of the change in the intensity of both reflected and scattered light; FIG. 3 shows a dew point meter that measures the water content on the basis of the change in the intensity of scattered light; and FIG. 4 shows another dew point meter that measures the water content on the basis of the change in the intensity of scattered light. The number of types of dew point meters available today is very great and those shown in FIGS. 1–4 are for illustrative purposes only and are by no means intended to limit the applicable scope of the present invention.

The practice of the present invention is described below briefly with particular reference to FIGS. 1–4.

A method of practicing the present invention is first described below with reference to FIG. 1. A multi-stage thermoelectric freezer 1 is provided to control the temperature of a reflector mirror 10 and to make it possible to decrease the temperature down to $-80°$ C. and below. Shown by 2 is a light source/lens combination. The light collected by the lens will always be projected towards the reflector mirror 10 and the light reflected by the mirror is received by a photodetector 4 equipped with a condenser lens. The intensity of that light is measured with detection mechanism 3 and is thereafter amplified with amplifier 7 and converted by means of D/C converter 8 for controlling the cooling capacity of freezer 1. A sample gas to be measured is supplied into the cell C of the dew point meter via an inlet 5 and discharged through an outlet 6 as it makes contact with the reflector mirror 10. If the temperature of the reflector mirror 10 is slowly reduced to have dew or frost condensed on the mirror surface, the intensity of the light being collected by the photodetector 4 will decrease by a sufficient amount to enable the dew point to be determined on the basis of an output 9 from a resistance thermometer or a thermocouple. Further, on the basis of the condensation of dew or frost as sensed by the detection mechanism, the thermoelectric device is heated so that the water on the reflector mirror is evaporated. After sensing the decrease in the water content with the photodetector 4, the thermoelectric freezer 1 is cooled by the same method. This method which performs continuous measurement of the dew point by a feedback system is already known in the art. A problem with this method is that the sample gas to be measured contains not only water but also particles including oils, metal oxides, metal powders, soot, salts and organic compounds; if such particles build up on the surface of the reflector mirror 10, the correct measurement of dew point cannot be assured. In this case, the thermoelectric freezer 1 will continue heating the reflector mirror in response to the feedback mechanism and, as a result, the measured dew point will be on the higher side, thus producing an abnormal error. Of course, the reflectance of the reflector mirror 10 can be restored to some extent by heating it to a certain level, say, room temperature. Subsequently, a $CO_2$ gas is introduced through the inlet 5, brought into contact with the reflector mirror in the cell C and discharged through the outlet 6. Thereafter, the reflector mirror is cooled to $-80°$ C. with the thermo-electric freezer 1 so that $CO_2$ is condensed on the surface of the reflector mirror 10 since the subliming point of $CO_2$ is $-78.5°$ C. at one atmosphere pressure. In the next place, the reflector mirror 10 is heated with the thermo-electric freezer 1 to vaporize the $CO_2$ on the surface of the mirror 10 and maintain the temperature between $-50°$ C. and room temperature. The above-described procedure is repeated from two or five times, preferably three times, whereby all the impurities other than water that are present on the surface of the reflector mirror can be readily discharged to the outside of the equipment through the outlet 6 when the $CO_2$ gas is vaporized.

FIG. 2 shows a dew point meter that is capable of measuring the dew point or frost point more precisely on the basis of the change in the intensity of both reflected and scattered light. Shown by 11 is a multi-stage thermoelectric freezer which is capable of varying the temperature of a reflector mirror 20. Shown by 12 is a light source furnished with a condenser lens. Shown by 14 is a detector assembly in which reflected light as collected by a condenser lens is detected with a light-receiving LED, and 13 is a detector assembly in which scattered light as collected by a condenser lens is detected with a light-receiving LED. Shown by 21 is an inspection window. Shown by 18 is the housing of the entire apparatus. A sample gas to be measured is supplied through an inlet 15 and enters cell C after it is preliminarily cooled with a precooler 17 by less than a hundred degrees Celsius if the dew point of the gas is lower than $-60°$ C. The supplied gas makes contact with the surface of the reflector mirror 20 and is thereafter discharged through an outlet 16. If dew or frost occurs on the surface of the reflector mirror 20, the intensity of the light received by the detector 14 decreases whereas the intensity of the light received by the detector 13 increases; hence, the corresponding temperature can be readily detected with the thermometer 19 to determine the dew point or frost point of the sample gas, as in the case shown in FIG. 1. Another approach that can be taken is as follows: dew or frost is first condensed on the surface of the reflector mirror; then, on the basis of the changes in the outputs of detectors 13 and 14, the freezer 11 is operated to either heat or cool the reflector mirror so as to perform continuous measurement of the dew point or frost point of the sample gas. Even if frost or dew is vaporized from the surface of the mirror 20, the occurrence of significant systematic errors is unavoidable in continued successive measurements of the dew point or frost point unless the reflectance of the mirror 20 that has dropped as a result of the deposition of particles is completely restored to the initial level, and there will be no particular need to make further explanation of this possibility. In this case, too, the reflectance of the mirror 20 can be restored to the initial level in an easy and complete way by introducing a $CO_2$ gas through the inlet 15 as in the method taken with the dew point meter shown in FIG. 1.

FIG. 3 shows an example of the method of determining the dew point of a sample gas, particularly a gas having a dew point lower than −80° C., solely on the basis of the change in the intensity of scattered light. Although not shown, the freezer may either be a helium refrigerator or adopt liquid nitrogen as a freeze source. Shown by 1a is a heat conductor that cools a cold head 20c as assisted by the cooling capacity of the freezer, and 8a is a heater that is used to control the cooling rate or to heat the cold head 20c. Shown by 10c is a reflector mirror, whose temperature can be freely varied with the heater 8a. A thermometer 19c is generally made of a platinum resistor and inserted in an area near the reflector mirror 10c. Cell C consists of two divided parts, one being on top of the other. The upper part 3a is typically made of a good heat conductor such as gold, silver, copper, aluminum, silicon, nickel or chromium, whereas the lower part 7a is made of a poor heat conductor such as stainless steel, Cu—Ni alloy, ceramics, glass or plastics.

Shown by 8a' is a heater, and 20c' is a temperature sensor. These devices help the temperature of the upper part 8a of cell C to be controlled freely. A sample gas to be measured enters cell C via inlet 5a. The part of the line that penetrates the cell wall and the subsequent portion is made of a thin-walled stainless steel tube and, in cell C, the gas is blown against the reflector mirror 10c on the bottom of the cell, from which the gas is discharged through a gas outlet 6a. To increase the response speed, the gas line is desirably composed of a tube of a suitable material, such as a special dry $O_2$ passivated stainless steel, that has a diameter of ¼", ⅛", ¹⁄₁₆" etc., that has been electropolished or otherwise treated to provide a smooth inner surface, and that is subjected to less adsorption or desorption of water and water release from the interior.

The light from the light-emitting diode (LED) 2a is sufficiently focused to illuminate a limited area of the surface of the reflector mirror 10c. To determine the point of dew or frost condensation on the surface of the reflector mirror, the change in the intensity of scattered light is detected with a PN photodiode with a condenser lens that is positioned in a direction exterior to the angle of reflection of the light projected from the LED 2a. The temperature at that time is measured with the temperature sensor 19c'. At the same time, the circulating helium refrigerator (not shown) is shut down but the reflector mirror is heated after the heater 8a is turned on. Alternatively, the helium refrigerator is not shut down but the heater 8a is controlled to freely adjust the temperature of the reflector mirror 10c.

Cold portions such as cell C, the freeze transmitting part 1a of the helium refrigerator and the cold head 20c must be thermally isolated from the ambient air, and vacuum or appropriate heat insulation is necessary.

Even in the case of a frost point meter of the type described above which is especially intended for measuring dew points lower than −80° C., it is possible to clean the surface of reflector mirror 10c by supplying $CO_2$ through gas inlet 5a as in the dew point meters shown in FIGS. 1 and 2.

Another embodiment of the present invention is shown in FIG. 4. Shown by 1b is a freeze generator; 8b is a heater; 20b is a cold head; the wall 3b of component A is made of a good heat conductor such as gold, silver, copper, aluminum, silicon, nickel or chromium; 5b is an inlet for supplying a sample gas to be measured; compartment B is surrounded by a wall 7b, with a hole 9b being formed in the wall at the interface between compartments A and B; 10b is a reflector mirror positioned to cover the hole 9b. Shown by 11b is the gap between the reflector mirror 10b and the inner surface of the wall 3b of compartment A. The gap 11b is preferably as small as possible but if it is designed to be extremely small, the slightest manufacturing error can potentially cause the reflector mirror 10b to contact the inner face of the wall 3b. To avoid this possibility, the gap preferably has a size of 0.1–2.0 mm. At least a part of the wall 7b of compartment B is made of a poor heat conductor such as stainless steel, a Cu—Ni alloy, glass, ceramics or plastics (e.g., a fluorine resin, a polyimide resin and a silicone resin). This is in order to insure that compartment A will not be chilled by the cold head 20b. Shown by 6b in FIG. 4 is a gas outlet; 2b is a light source furnished with a condenser lens and 2b may be a light-emitting diode emitting at a given wavelength; 4b is a photodetector equipped with a condenser lens.

A measurement of the water content of a gas with the apparatus shown in FIG. 4 will proceed as follows. First, the gas to be measured is supplied through the inlet 5b into compartment A which is controlled at a given temperature by means of heater 8b' and temperature sensor 19b' inserted in the wall 3b of compartment A; the gas flows through the hole 9b to make contact with the reflector mirror 10b, and the water present in a very small amount in the gas will form dew or frost on the reflector mirror 10b. The uncondensed gas passes through the gap 11b to be discharged from compartment B through the outlet 6b; the gap 11b is small enough to insure that the gas flowing from compartment A to compartment B through the hole 9b will not fail to contact the reflector mirror 10b; the light from the light source 2b is illuminated in such a way that it is concentrated by the detector 4b with a condenser lens to be focused at the dew or frost layer formed on the reflector mirror 10b, and the dew point or frost point is evaluated by measuring the change in the intensity of scattered light due to dew or frost with the detector 4b and the dew point or frost point is measured with a detector unit (not shown). In this case, too, the fouling at the surface of reflector mirror 10b due to foreign matter will change the absolute value of the intensity of scattered light during proposed use, whereby an error is introduced in the measurements of dew point and/or frost point. If this is anticipated to occur, $CO_2$ or a $CO_2$ containing gas may be introduced through inlet 5b either manually or automatically so that $CO_2$ is either condensed on the mirror 10b and vaporized therefrom. By repeating this cycle several times, the reflectance of the mirror can be easily restored to the initial level.

A helium refrigerator (not shown) may typically be used in the freeze generator but other freezing media such as liquefied nitrogen may also be used.

In the apparatus shown in FIG. 4, compartment A preferably has an inner capacity of 0.5–5 cm$^3$. Compartment A may have any shape as seen in plan view.

In FIG. 4, compartment A is shown to be positioned above compartment B. Inversely, compartment B may be positioned above compartment A. If desired, both compartments A and B may be juxtaposed on a horizontal plane.

Figure 5:
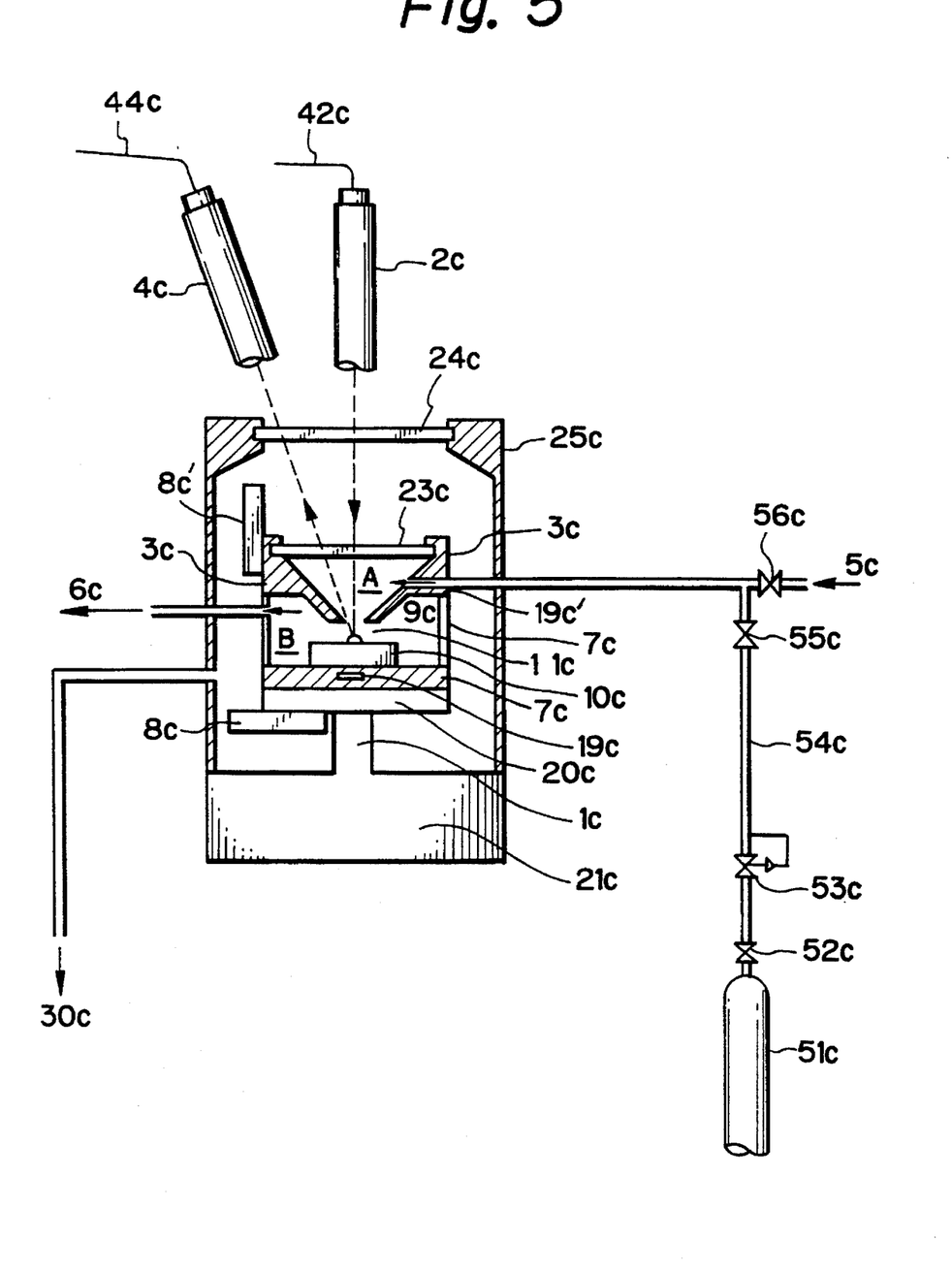
FIG. 5 is a diagram showing an apparatus according to another preferred embodiment of the present invention.

Still another embodiment of the present invention is shown in FIG. 5. Shown by 21c is a freeze generator and 1c is a heat conductor. Shown by 8c is a heater, and 20c is a cold head. The measuring cell consists of compartments A and B. Wall 3c of compartment A may typically be composed of a good heat conductor such as gold, silver, copper, aluminum, silicon, nickel or chromium, and wall 7c of compartment B is chiefly composed of a poor heat conductor such as stainless steel, Cu—Ni alloy, glass, ceramics or plastics (e.g., fluorine resins, polyimide resins and silicone resins). Shown by 23c and 24c are each a window made of a light-transmissive material such as glass. Shown by 5c is an inlet for introducing a sample gas to be measured. Shown by 10c is a reflector mirror; 6c is a gas outlet; 2c is a condenser lens for condensing light from a light-emitting diode or the like so that it can be radiated towards the reflector mirror; 4c is a condenser lens for collecting the scattered light from the reflector mirror 10c so that it is sent to a photodetector. Shown by 42c and 44c are each an optical fiber.

Windows 23c and 24c are made of a light-transmissive material such as glass. A nozzle of gentle slope is provided at the interface 9c between compartments A and B. Provided beneath the nozzle 9c is the reflector mirror 10c in such a way that the latter will cover the nozzle. Indicated by 11c is the gap between the reflector mirror 10c and the nozzle 9c. The gap 11c is preferably as small as possible but if it is designed to be extremely small, the slightest manufacturing error can potentially cause the reflector mirror 10c to contact the nozzle 9c. To avoid this possibility, the gap preferably has a size of 0.1–2.0 mm.

A measurement of the water content of a gas with the apparatus shown in FIG. 5 will proceed as follows. First, the gas to be measured as supplied at inlet 5c is introduced through valve 56c into compartment A which is controlled at a given temperature by means of heater 8c' and temperature sensor 19c'; the gas flows through the nozzle 9c to make contact with the reflector mirror 10c, and the water present in a very small amount in the gas will form dew or frost on the reflector mirror 10c. The uncondensed gas passes through the gap 11c to be discharged from compartment B through the outlet 6cthe gap 11c is small enough to insure that the gas flowing from compartment A to compartment B through the nozzle 9c will not fail to contact the reflector mirror. The light is illuminated in such a way that it is concentrated by the condenser 2c to be focused at the dew or frost layer formed on the surface of the reflector mirror 10c and the change in the intensity of scattered light due to dew or frost formation is transmitted to a detector mechanism via the condenser lens 4c and the optical fiber 44c, whereby the dew point or frost point of the gas is evaluated. The temperature at that time is measured with a temperature sensor 19c.

Shown by 51c in FIG. 5 is a cylinder filled with liquefied $CO_2$ gas having a five-nine grade quality. Shown by 52c is a main valve on the cylinder; 53c is a pressure regulating valve; 54c is a pipe; and 55c is a stop valve.

Usually, $CO_2$ gas is available on the market as 99–99.9% concentrated liquefied gas in a cylinder, but $CO_2$ is also available in the form of recovered gas. In particular, when measuring low dew points (e.g., lower than −100° C. such as −110° C. and −120° C.), it is not absolutely necessary to use nearly 100% $CO_2$ with the frost point meter. This is because $CO_2$ can be condensed at lower temperatures that correspond to the low partial pressure of $CO_2$. Hence, the gas to be supplied may contain $N_2$, Ar, He, air or other impurities in addition to $CO_2$ but the presence of oils and dust or dirt particles is not preferred. Thus, when using ordinary $CO_2$ gas or $CO_2$ containing gas, it is necessary to install a properly designed purifier as an additional apparatus.

Figure 6:
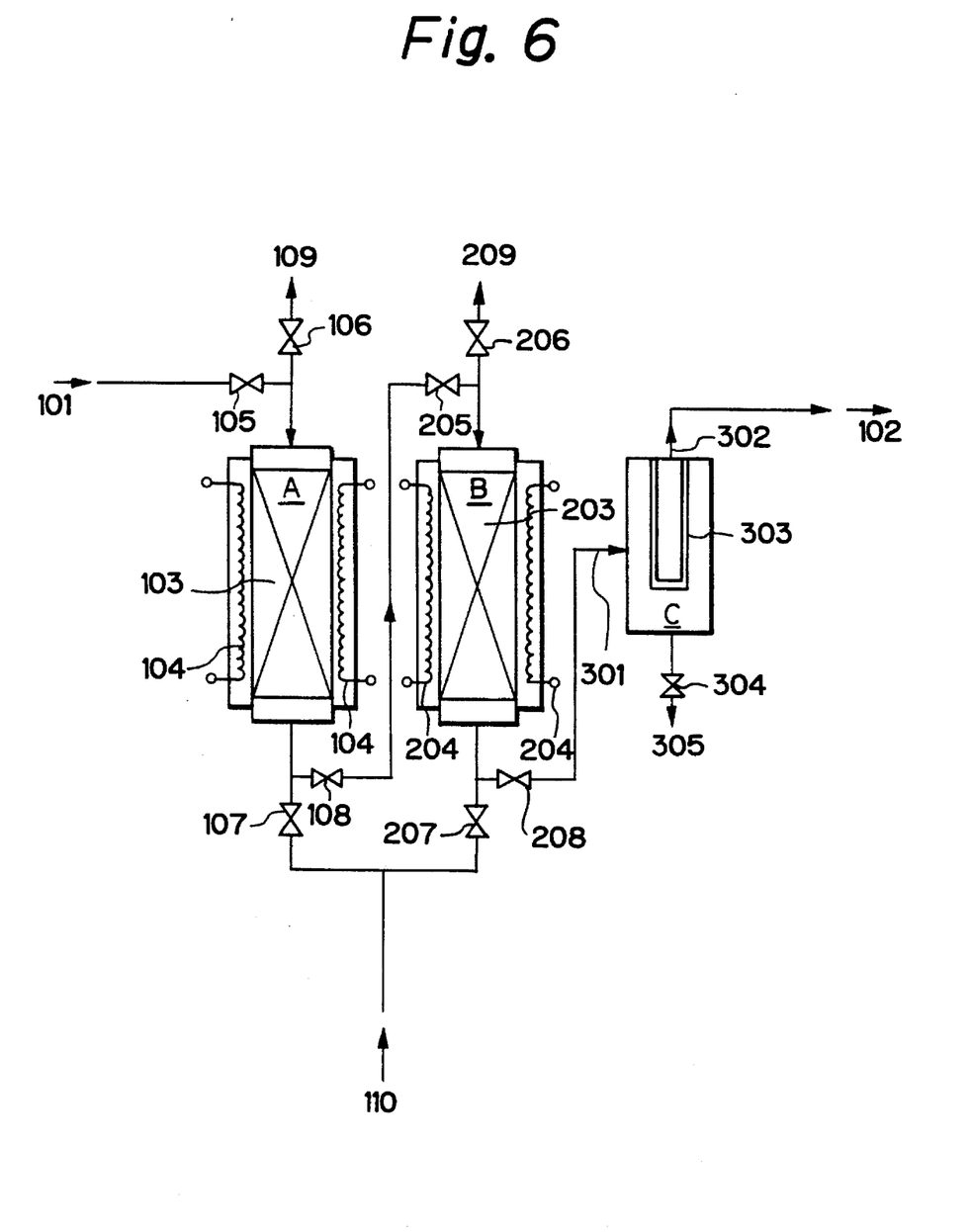
FIG. 6 is a diagram showing an apparatus according to yet another preferred embodiment of the present invention.

FIG. 6 illustrates a $CO_2$ purifier that may be adopted to this end. Cylinder A is a drying cylinder packed with a molecular sieve, an alumina gel or a mixed bed thereof such as 3A, 4A or 5A, and cylinder B is packed with activated carbon. Cylinder C uses a filter having the ability to trap particles with a size of at least 0.1 μm. The filter element is preferably made of a ceramic material or a stainless steel fiber.

The apparatus shown in FIG. 6 is used in the following manner. First, an inert gas of the highest possible purity that is prepared by vaporizing liquid nitrogen is introduced at 110 while valve 105 is closed and valves 107, 106, 207, 208, 206, 305, 108 and 205 are opened so that a dry nitrogen gas is allowed to flow through cylinders A, B and C to clean them. After it is verified that these systems have been completely purged with the dry nitrogen gas, valves 108, 205, 208 and 304 are closed. Then, cylinders A and B are heated with heaters 104 and 204. Cylinders are preferably heated to 300°–350° C., more preferably to 350° C. By supplying a dry $N_2$ gas, at least the alumina gel or molecular sieve 103 in cylinder A and the activated carbon 203 in cylinder B are heated. After the end of heating, heaters 104 and 204 are turned off and cylinders A and B are cooled to room temperature by the flow of a $N_2$ gas. Thereafter, valves 106, 107, 207 and 206 are closed whereas valves 105, 108, 205 and 208 are opened, so that a $CO_2$ containing gas is supplied at 101 and delivered from 102 to be introduced into various types of dew point meter.

The $CO_2$ introducing mechanism is shown only in FIG. 5 but it should be noted that a similar method may be adopted in other cases. Instead of $CO_2$ of a five-nine grade purity, ordinary commercial cylinders may be used and, in this case, 5ac, 52c and 53c are connected with 101 in FIG. 6 and the gas is adjusted to a near-atmospheric pressure by means of 53c. After passing it through the purifier shown in FIG. 6, the outlet at 102 is connected to the pipe 54c for starting the operation. The $CO_2$ gas which passes through the purifier shown in FIG. 6 will thereby be preliminarily purified by removal of water, oil and particles.

EXAMPLE

By the method shown in FIG. 5, it was verified that the intensity of scattered light had reached 1000 mV on account of the fouling of the surface of a reflector mirror and under such conditions that the temperature was ambient, with neither dew nor frost condensed. Thereafter, commercial 99.94 pure liquefied $CO_2$ gas was further purified by The method shown in FIG. 6. The thus purified $CO_2$ gas condensed on the surface of the reflector mirror at a temperature of ca. −80° C., with the mirror being then heated up to room temperature. By repeating this cleaning procedure, the following data were obtained: 200 mV at the first cleaning cycle; 180 mV at the second cycle; 175 mV at the third cycle; and 170 mV even at the fourth cycle. These data were in substantial agreement with the results obtained by cleaning in the same manner before shipment from the factory.

If the reflector mirror is cooled to below −78.5° C. during the cleaning operation conducted in accordance with the present invention, $CO_2$ will be condensed as frost on the mirror surface at the temperature corresponding to the partial pressure of $CO_2$. By subsequent heating with the heater, oils and particles on the mirror are dssolved with $CO_2$ so that they are discharged from the system by evaporation together with $CO_2$. Preferably, this procedure is repeated 3–4 times. A measurement can be resumed right after this cleaning operation.

The method of the present invention can be practiced on the site and requires no special skill for maintenance operations.

The present invention is particularly effective in the case where dew point or frost point measurements are to be performed continuously or in the case where they are intermittent with the temperature at the surface of the reflector mirror being continuously held near the dew point or frost point of a gas to be measured. When measuring the low water content of a gas at temperatures below −80° C., the fouling of the surface of a reflector mirror will cause substantial effects on the precision and sensitivity of measurement, so cleaning the mirror surface after detecting the degree of its fouling is important. High-purity $N_2$, Ar, $O_2$, He, $H_2$ and other gases that have frost points lower than −90° C. are specially used in the process of semiconductor fabrication and they are required to have a very low water content of 1 ppb (equivalent to a frost point of −110° C.). The basic method for the practice of the present invention which is to be applied to this purpose is to determine the dew point or frost point of a gas containing a very small amount of water using an optical dew point meter including a reflector mirror the temperature of which can be varied from room temperature to any point of down to −80° C., a means of contacting said reflector mirror with the gas to be measured, a means Of irradiating said reflector mirror with focused rays of light and/or laser light, and a means of detecting the change in scattered light and/or reflected light due to the dew and/or frost condensed on said reflector mirror, said method comprising the steps of:

contacting said reflector mirror with the gas to be measured;

applying said focused rays of light and/or laser light onto that part of the reflector mirror where it is contacted with said gas;

gradually reducing the temperature of said reflector mirror, either before or while said reflector mirror and said gas contact, thereby condensing dew and/or frost on said reflector mirror; and gradually elevating the temperature of said reflector mirror to a point in the neighborhood of the dew point and/or frost point but which is insufficient to have the dew and/or frost sublime completely from the mirror surface, thereby detecting the temperature at which the scattered light has a maximum intensity and/or the temperature at which the reflected light has a minimum intensity, or again cooling the reflector mirror to detect the temperature at which the scattered light has a minimum intensity and/or the temperature at which the reflected light has a maximum intensity, and designating said maximum and minimum temperatures as the dew point and/or frost point of the gas of interest.

Preferably, the temperature of said reflector mirror is gradually reduced or elevated by cooling or heating said reflector mirror at a rate that is varied either stepwise or continuously generally along the curve represented by:

$$R(T)=R(T_O)[P'(T)/P(T_O)]^n \qquad (1)$$

where

T: the temperature (K) of the reflector mirror;

$T_O$: any specific temperature (K) that can be selected from the range of from room temperature to the temperature of liquid nitrogen;

R(T): the cooling and/or heating rate (K/min) at a selected temperature (K) of the reflector mirror;

P'(T): the derived function of the saturated vapor pressure of ice determined with the temperature (T) being taken as a variable;

$P'(T_O)$: a calculated value of the saturated vapor pressure of water at the specific temperature $T_O$; and n: the value so selected as to provide a substantially constant signal-to-noise ratio of at least 2 in the measurement of the change in reflected light and/or scattered light over a fixed temperature interval ΔT.

For the sake of simplicity, the following description concerns only the scattered light (the reflected light is the same as the scattered light except that the variation in intensity is reversed).

The operating principle of the method under consideration is described below with reference to FIG. 7 and FIG. 7'.

Figure 7:
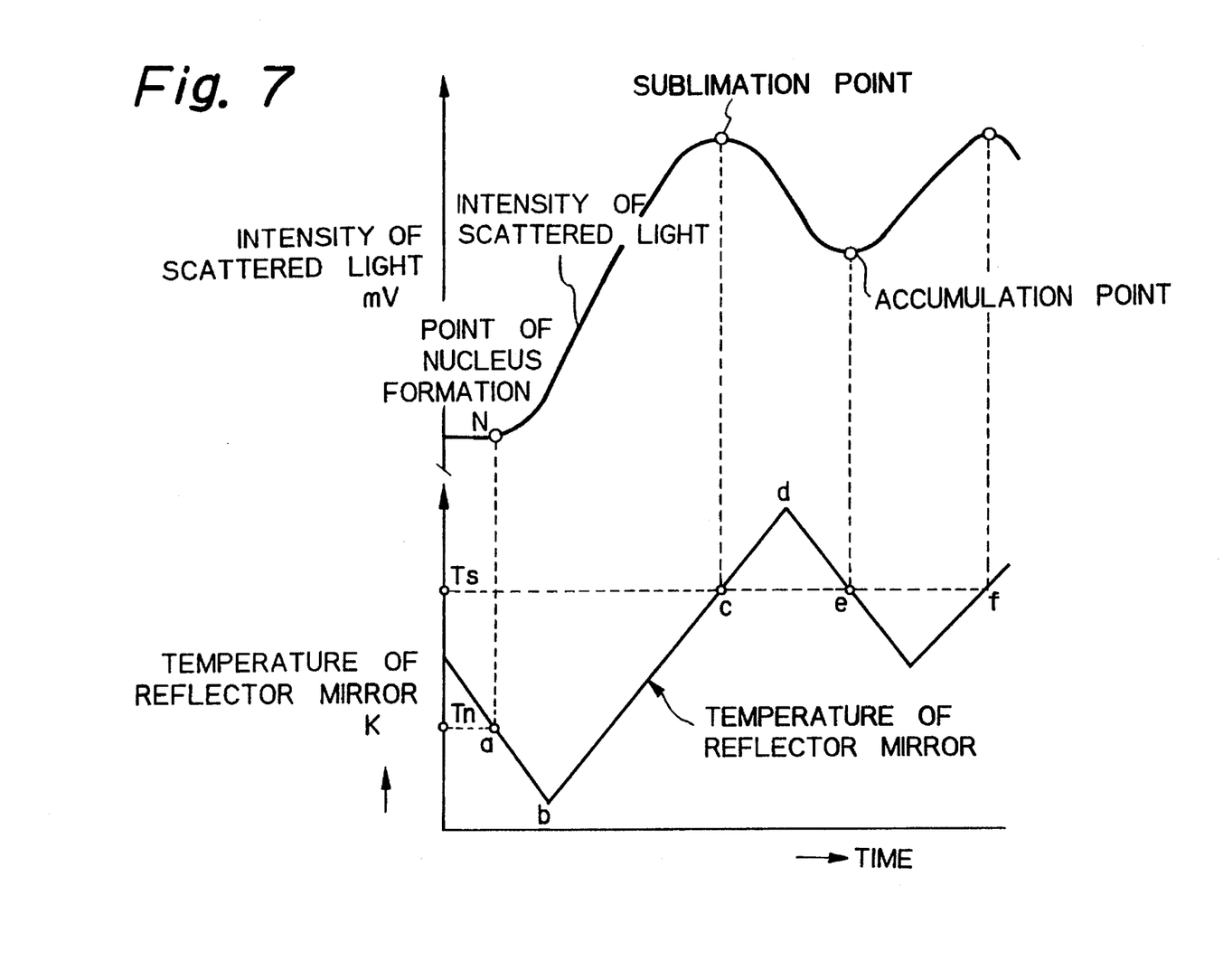
FIG. 7 and FIG. 7' are graphs showing the relationship between the change in the temperature of a reflector mirror and the intensity of scattered light.

In regard to FIG. 7, suppose that the temperature of the reflector mirror is lowered; then, dew or frost condensation occurs at point a. However, the gas is highly likely to be suppercooled, so point a does not correspond to the correct dew or frost point. The temperature is further lowered and if one is sure that the nucleus forming point has been reached at point b, the temperature is thereafter elevated. Needless to say, the gas in this state is suppercooled and the ice will continue to grow. Point c where the intensity of scattered light is at a maximum may be designated the sublimation point. The temperature of the reflector mirror at the point corresponds to $T_S$. Then, the reflector mirror is heated up to point d which can be regarded as the sublimation point, whereupon the ice starts to vaporize and the temperature of the reflector mirror starts to decrease at point d downward until the intensity of scattered light attains a minimum level at point e. The temperature at that point, or the accumulation point, also corresponds to $T_S$. Thus, it has been verified that the sublimation point where the amount of light reception takes on a maximum value and the next occurring accomulation point agree to each other for a gas of the same water content; hence, one may safely conclude that $T_S$ corresponds to the correct dew or frost point of the gas of interest. If the cycle of heating or cooling the reflector mirror is repeated, the curve for the scattered light will also change drawing a parabolic pattern. The sublimation point and the accumulation point occur cyclically.

Profiles for the cooling and heating rates in the case under consideration are given below.

TABLE 1

| Cooling Rate | |
| --- | --- |
| Temperature range (°C.→°C.) | Cooling rate (°C./min) |
| 20 −70 | 10.0 |
| −70 −90 | 4.0 |
| −90 −100 | 2.0 |
| −100 −105 | 1.0 |
| −105 −110 | 0.5 |

TABLE 1-continued

Cooling Rate

| Temperature range (°C.→°C.) | Cooling rate (°C./min) |
| --- | --- |
| −110 −115 | 0.25 |
| −115 −120 | 0.13 |
| −120 −125 | 0.063 |
| −125 −130 | 0.031 |
| −130 −135 | 0.016 |

TABLE 2

Heating Rate

| Temperature range (°C.→°C.) | Heating rate (°C./min) |
| --- | --- |
| −135 −130 | 0.016 |
| −130 −125 | 0.031 |
| −125 −120 | 0.063 |
| −120 −115 | 0.13 |
| −115 −110 | 0.25 |
| −110 −105 | 0.5 |
| −105 −100 | 1.0 |
| −100 −90 | 2.0 |
| −90 −70 | 4.0 |
| −70 30 | 10.0 |

Equation (1) is a formula for a curve. The lower the temperature, the slower the heating and cooling rates. In the case under consideration, the rate of cooling from 20° C. to −70° C. is 10.0° C./min where as the rate of cooling from −130° C. to −135° C. is 0.016° C./min. If it is assumed that cooling or heating is conducted following the curved path represented by Equation (1), the heating or cooling rate must be slowed down at decreasing temperature and to achieve this, performing a fully computer-aided control is ideal. However, this approach is not economical.

The common practice is to lower the cooling or heating rate stepwise as shown in Tables 1 and 2 above. For example, at temperature below −100° C., the cooling or heating rate is varied for every decrement of 5° C.

In regard to FIG. 7 , this figure helps explain how the fouling of the mirror is detected in the present invention. In FIG. 7', the curve indicted by the dashed line is identical to the curve for plotting the intensity of scattered light in FIG. 7. The solid line refers to the case where the reflector is free from fouling. As the mirror becomes progressively fouled, the left side of the curve deforms as indicated by the sequence of dashed lines (a)–(e). The curve indicated by dashed line (e) refers to the most foul state of the mirror. If the mirror is clear, the intensity of scattered light is 200 mV at the start of measurement; in contrast, if the mirror is very foul (curve e), the intensity is 5,000 mV at the start of measurement. This is how it is possible to detect the fouling of the mirror in the present invention.

Figure 8:
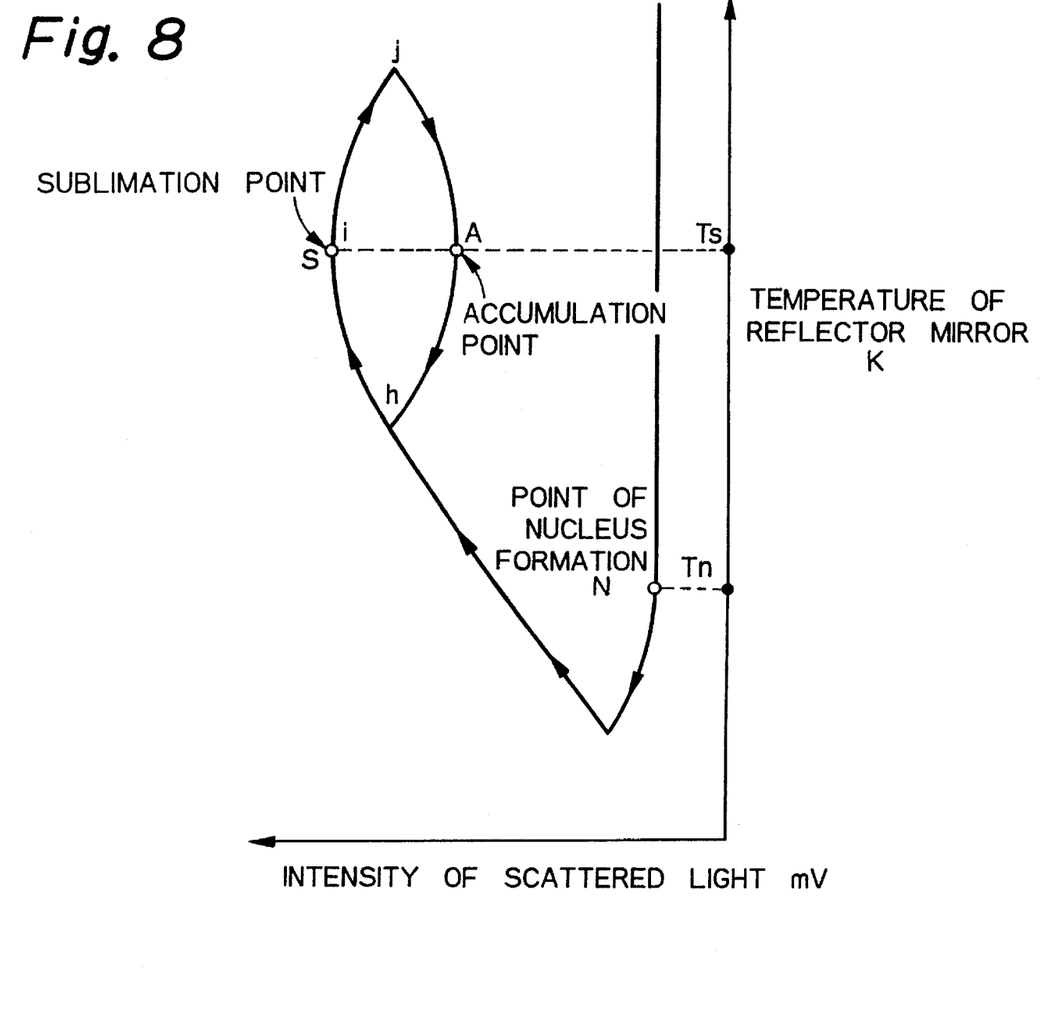
FIG. 8 is a graph showing, in association with FIG. 7, the relationship between the intensity of scattered light and each of the nucleus forming point, the subliming point and the accumlation point.

FIG. 8 is a graph showing the relationship between the temperature of the reflector mirror and the intensity of scattered light with respect to a similar expriment.

When the cycles of heating and cooling the reflector mirror are repeated, the intensity of scattered light changes drawing a parabolic curve to form a loop as shown in FIG. 8.

Figure 9:
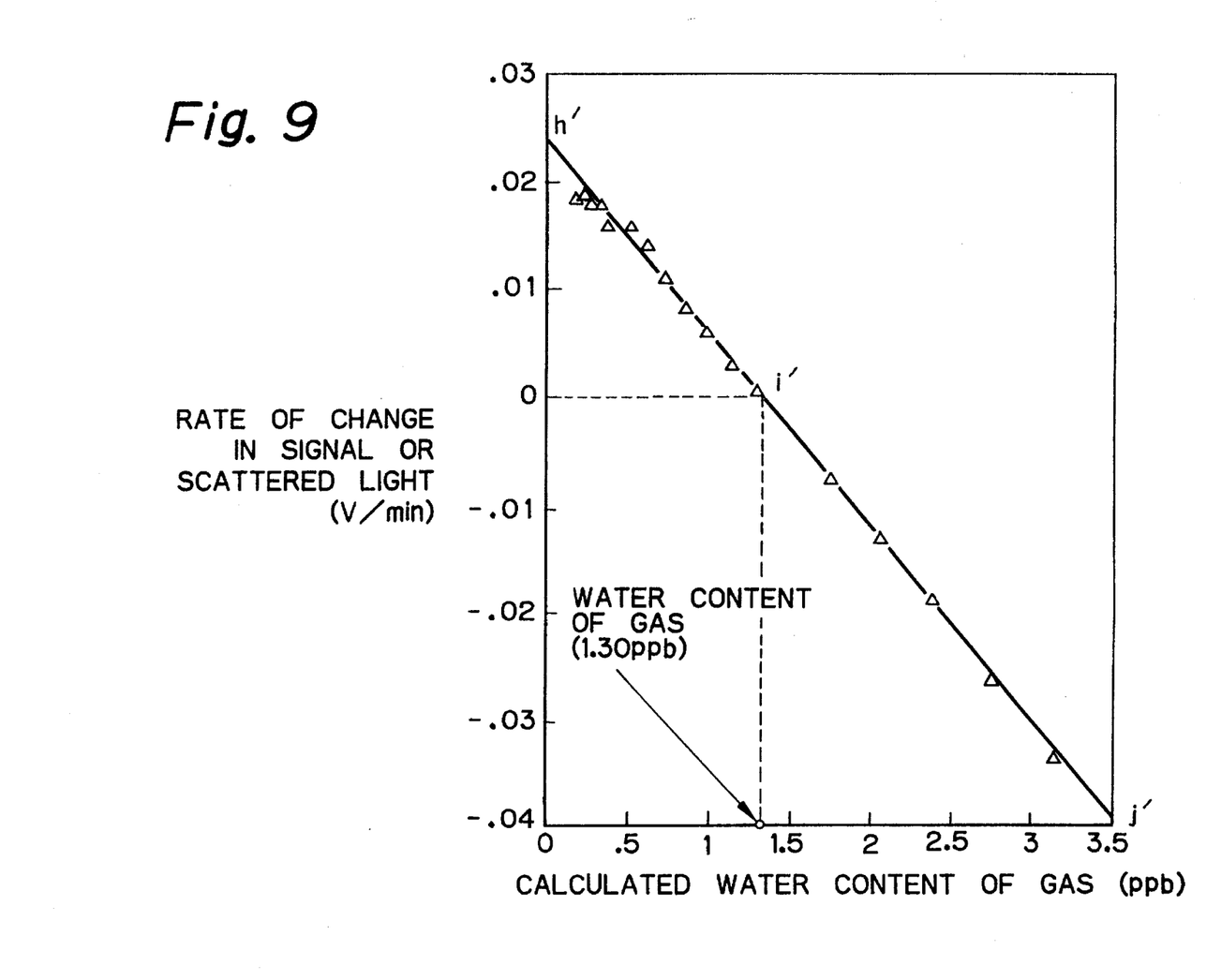
FIG. 9 is a graph illustrating the method by which the relationship shown in FIG. 8 is differentiated to construct a straight line and the water content is determined from a maximum value showing the occurrence of sublimation.

FIG. 9 is a graph showing the relationship between the water content of a particular gas and the relative change in a signal for scattered light. Referring back to FIG. 8, the intensity of scattered light changes at points h, i and j drawing a curve when the temperature of the reflector mirror is varied. Assuming that the curve connecting points h, i and j represents a quadratic function, one may differentiate it and plot the result on a straight line, as shown in FIG. 9. In FIG. 9, points h', i' and j' correspond respectively to points h, i and j in FIG. 8. The water content of the gas as plotted on the horizontal axis represents the value as determined from the equation for the vapor pressure of ice.

One may safely conclude that the gas under consideration had a water content of 1.30 ppb. The conditions of the experiment were as follows:

$T_o = -90°$ C.

$R(T) = $ ca. 4° C./min $n = $ ca. 0.67

$\Delta T = $ ca. 0.4° C.

Sample measured once for every two seconds.

Another characterizing part of the present invention is that it makes a special provision for the error resulting from noise that will unavoidably occur in measurements of the type contemplated by the present invention. If the peak intensity of scattered light is taken as the point of dew or frost condensation, noise makes it very difficult to read the correct point. However, if the point of dew or frost condensation is to be derived from the crest of a peak of the bottom of a valley as in the present inveniton, one may plot the actual points on the straight line obtained by differentiating a quadratic curve and determine the point of dew or frost condensation at the crest of a peak on the straight line obtained by the method of least squares. This insures the operator to obtain very precise and stable values even in the presence of noise.

Figure 10:
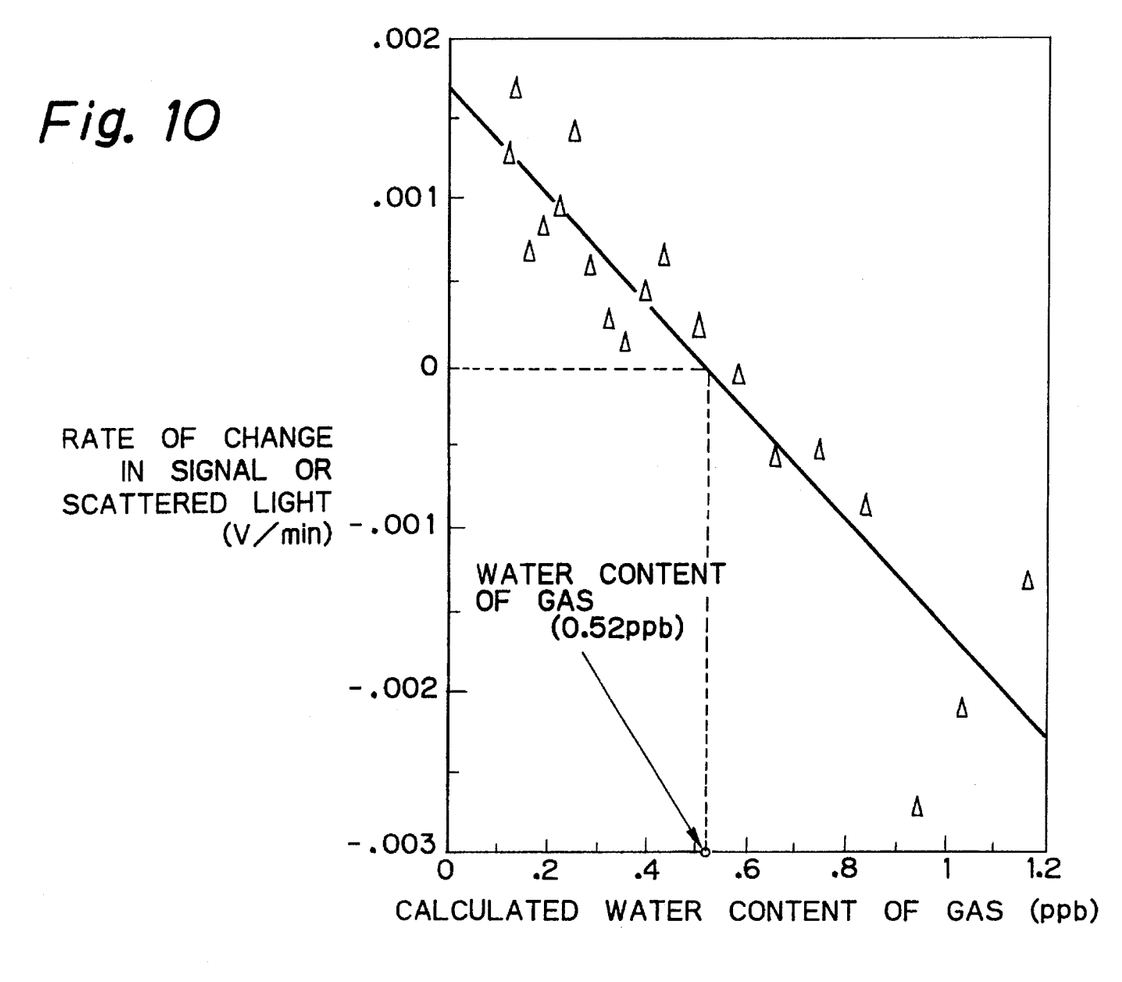
FIG. 10 is a graph showing the effect of background noise on determination of the water content by the same method as shown in FIG. 9.

FIG. 10 illustrates the case where background noise was so great as to cause considerable variations in the results of measurement. By making use of the straight line obtained by the method of least squares, it is possible to determine water content when the water content is very small and as low as 0.52 ppb. One of the advantages of this method is that although it took 5–6 hours in the prior art to cause a change from the point of frost condensation to the subliming point when the frost point was −115° C., it took only about 1 hour to cause a change from the subliming point to the next occurring point of accumulation. At the frost point −110° C., the measurement could be completed within 30 min. The gas flow rate in that case was 500 Nml/min.

JIS K 0512 ("Hydrogen") lists a table of conversion between dew point and water content down to −100° C. but it is of no help at temperatures below −100° C. The only alternative for conversion is to use a line of extrapolation from the curve for the saturated vapor pressure of water as constructed in the manner described above. The formula that is known to be the most reliable today is:

$$\log_{10} P_{H^2O} = -2445.5646/T + 8.2312 \log_{10} T - 0.01677006T + 1.20514 \times 10^{-5} T^2 - 6.757169$$

$$C = P_{H^2O}/760.10^9$$

where

T: dew point on the absolute scale (K)

$P_{H^2O}$: the saturated vapor pressure of water (mmHg)

C: water content (ppb)

This formula is given in International Critical Tables of Numerical Data, Physics, Chemistry and Technology, Volume III, p. 210, National Research Council of USA (1928). The water content data as plotted in FIGS. 9 and 10 were obtained by computation from the measured values of subliming point and point of condensation of the topmost layer.

A problem with the method, although intermittent, that measures the subliming point and the point of solidification of the topmost layer with ice being always present on the reflector mirror no matter how small its amount may be is that foreign matter other than ice, such as particles and oils, that are present on the reflector mirror can contaminate it. Needless to say, they will not affect the maxima and minima of the intensity of scattered and reflected light but there is no denying that they can influence the precision of measurements, namely, the resolution. If this occurs in the method under consideration, the slope of the straight lines drawn in FIGS. 9 and 10 will decrease as the degree of contamination increases. In order to insure correct measurements, the standard angle of inclination is predetermined for the case where the reflector mirror is in the normal state and it is cleaned with $CO_2$ if that angle is found to have decreased to an abnormally small value.

The method set forth in this example, which method references to FIG. 7, FIG. 7', FIG. 8, FIG. 9 and FIG. 10, provides means for sensing that the capability of detecting a normal change in the intensity of reflected light or scattered light has decreased on account of the fouling of the reflector mirror.

We claim:

1. In a method of cleaning a reflector mirror in an optical dew point meter that measures the dew point or frost point of a sample gas by a process including the steps of bringing the sample gas into contact with the reflector mirror whose temperature is variable, projecting condensed rays of light or laser light onto said reflector mirror, and detecting the change in the intensity of scattered light or reflected light on account of the dew or frost formed on said reflector mirror, characterized in that the cleaning steps of said method comprise the step of bringing $CO_2$ gas of five-nine grade purity, $CO_2$ gas or $CO_2$ containing gas, said $CO_2$ gas or $CO_2$ containing gas having been purified for removal of water, oils and particles, into contact with the reflector while the latter is in a cooled state, thereby condensing $CO_2$ on the surface of the reflector mirror, and the subsequent step of heating the reflector mirror to vaporize the $CO_2$.

2. A method according to claim 1 wherein said $CO_2$ containing gas comprises $CO_2$ and at least one gas selected from the group consisting of $H_2$, $O_2$, Ar, $N_2$, He, air and a mixture thereof.

3. A method of cleaning a reflector mirror in an optical dew point meter that measures the dew point or frost point of a sample gas into contact with the reflection mirror whose temperature is variable, projecting condensed rays of light or laser light onto said reflector mirror and detecting the change in the intensity of scattered light or reflected light on account of the dew or frost formed on said reflector mirror, characterized in that the cleaning steps of said method comprise the step of bringing $CO_2$ gas into contact with the reflector while the latter is in a cooled state, thereby condensing $CO_2$ on the surface of the reflector mirror, and the subsequent step of heating the reflector mirror to vaporize the $CO_2$ wherein the $CO_2$ gas used for cleaning is preliminarily purified by removing water, oils and particles.

4. An optical dew point meter equipped with a cleaning device, said meter comprising:
  (i) a reflector mirror whose temperature is variable;
  (ii) a gas inlet or a gas blowing nozzle for supplying a sample gas into a compartment including said reflector mirror in such a way that said sample gas will contact said reflector mirror;
  (iii) a means for protecting condensed rays of light to that part of the reflector mirror where dew or frost is to form;
  (iv) a means for detecting the change in the intensity of scattered light or reflected light due to the dew or frost formed on the reflector mirror;
  (v) a means for sensing that the capability of detecting a normal change in the intensity of reflected light or scattered light has decreased on account of the fouling of the reflector mirror;
  (vi) a means for causing $CO_2$ gas of five-nine grade purity, purified $CO_2$ or purified $CO_2$ containing gas to contact the reflector mirror either automatically or manually, said CO2 or CO2 containing gas having been preliminarily purified by removing water, oils and particles;
  (vii) a means for detecting the temperature at which the change in the intensity of scattered light or reflected light occurs, and
  (viii) means for controlling the temperature of said reflector mirror down to at least $-78.5°$ C.

5. An optical dew point meter equipped with a cleaning device, said meter comprising;
  (i) a reflector mirror;
  (ii) means for controlling the temperature of said mirror down to at least $-78.5°$ C.;
  (iii) a gas inlet or a gas blowing nozzle for supplying a sample gas into a compartment including said reflector mirror in such a way that said sample gas will contact said reflector mirror;
  (iv) a means for projecting condensed rays of light to that part of the reflector mirror where dew or frost is to form;
  (v) a means for detecting the change in the intensity of scattered light or reflected light or reflected light due to the dew or frost formed on the reflector mirror;
  (vi) a means causing liquefied $CO_2$ gas of five-nine grade purity, $CO_2$ or $CO_2$ containing gas to contact the reflector mirror either automatically or manually, said $CO_2$ or $CO_2$ containing gas having been preliminarily purified for removing water, oils and particles; and
  (vii) a means for detecting the temperature at which the change in the intensity of scattered light or reflected light occurs.

6. An optical dew point meter according to claim 5 wherein said meter further comprises a means for purifying the $CO_2$ or $CO_2$ containing gas.

* * * * *

UNITED STATES PATENT AND TRADEMARK OFFICE
CERTIFICATE OF CORRECTION

PATENT NO. : 5,470,154
DATED : November 28, 1995
INVENTOR(S) : Nishizawa et al.

It is certified that error appears in the above-indentified patent and that said Letters Patent is hereby corrected as shown below:

On the title page: Item [63] Continuation insert
-- which is a continuation of PCT/JP92/00493, filed
April 17, 1992, abandoned --.

Signed and Sealed this

Twenty-seventh Day of August, 1996

Attest:

BRUCE LEHMAN

Attesting Officer    Commissioner of Patents and Trademarks